United States Patent [19]
Haswell et al.

[11] Patent Number: 5,487,393
[45] Date of Patent: Jan. 30, 1996

[54] URINE SPECIMEN COLLECTION RECEPTACLE

[75] Inventors: James S. Haswell, Olathe; Michael S. Stevens, Lawrence, both of Kans.

[73] Assignee: Beckwell International, Inc., Olathe, Kans.

[21] Appl. No.: 192,590

[22] Filed: Feb. 7, 1994

[51] Int. Cl.⁶ ..................................... A61B 5/00
[52] U.S. Cl. .......................... 128/760; 128/736; 604/317; 604/318
[58] Field of Search .................... 128/736, 760, 128/761, 767; 604/317, 318

[56] References Cited

U.S. PATENT DOCUMENTS

| | | | |
|---|---|---|---|
| Re. 33,686 | 9/1991 | Parrish ........................ | 128/736 X |
| 3,774,455 | 11/1973 | Seidler et al. . | |
| 3,832,738 | 9/1979 | Kliemann ...................... | 128/761 X |
| 4,029,590 | 5/1977 | Wendt ......................... | 604/317 X |
| 4,070,912 | 1/1978 | McNaughton .................. | 128/736 X |
| 4,106,490 | 8/1978 | Spilman et al. . | |
| 4,408,905 | 10/1983 | Ehrenkranz .................... | 128/736 X |
| 4,466,445 | 8/1984 | Abrams ....................... | 128/736 |
| 4,554,687 | 11/1985 | Carter et al. .................. | 128/760 X |
| 4,564,299 | 1/1986 | Ehrenkranz . | |
| 4,769,215 | 9/1988 | Ehrenkranz . | |
| 4,832,046 | 5/1989 | Parish . | |
| 5,069,878 | 12/1991 | Ehrenkranz . | |
| 5,119,830 | 6/1992 | Davis . | |
| 5,181,905 | 1/1993 | Flam ........................... | 128/736 X |
| 5,222,809 | 6/1993 | Ehrenkranz .................... | 128/736 X |
| 5,282,683 | 2/1994 | Brett .......................... | 128/736 X |

Primary Examiner—Sam Rimell
Attorney, Agent, or Firm—Litman, McMahon and Brown

[57] ABSTRACT

A urine specimen collection receptacle is formed as a one-piece unit by vacuum forming a sheet resin and includes an outer rectangular trough forming a urine reservoir and a lid with a funnel formed therein. The lid is folded about a fold line into substantial covering relation to the trough with the funnel positioned within the reservoir and in fluidic communication therewith. Front corner areas of the trough have spout grooves formed therein, and corresponding areas at the front of the lid are beveled to facilitate pouring a collected sample into another container. The lid is provided with a bulged area to extend the volume of the reservoir to lessen the tendency of the sample to backflow through the funnel during pouring the sample to another container.

13 Claims, 2 Drawing Sheets

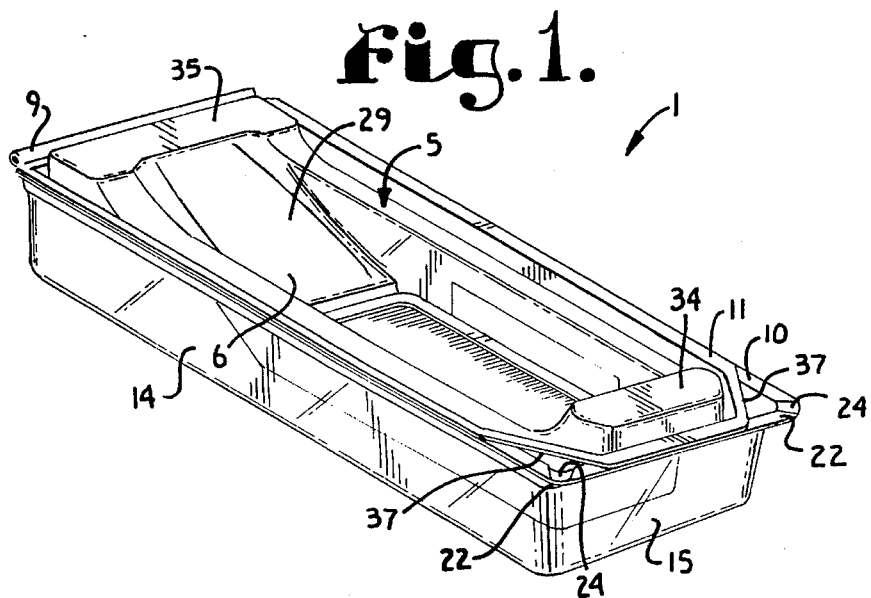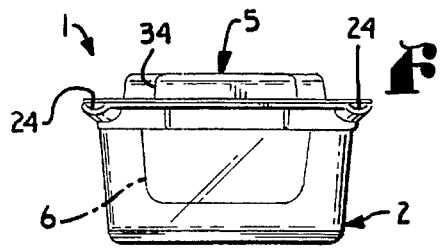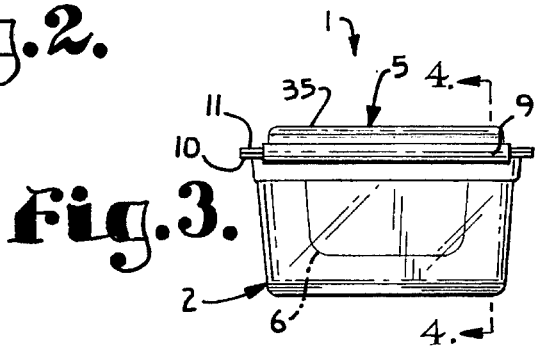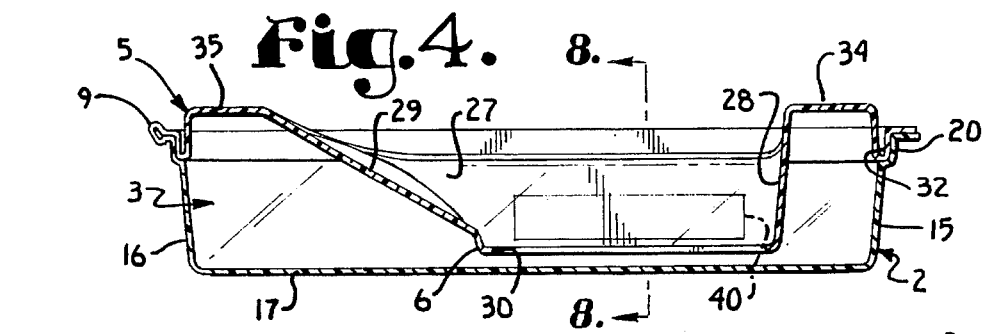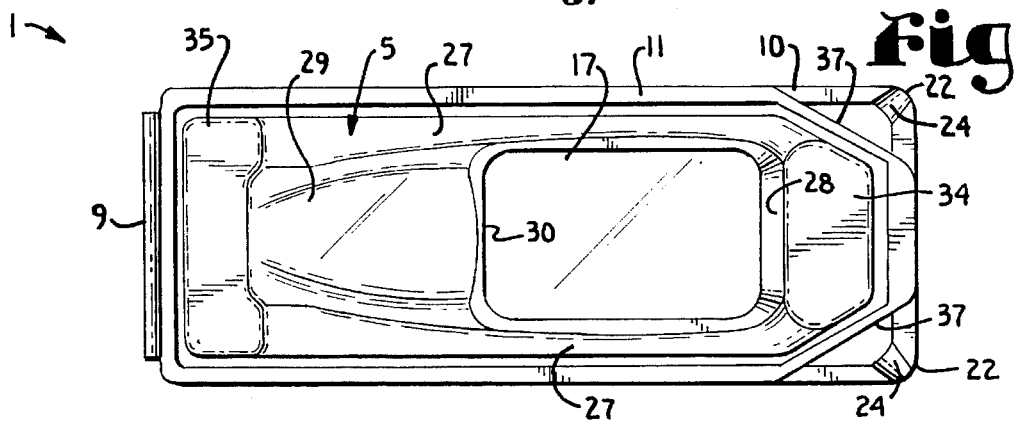

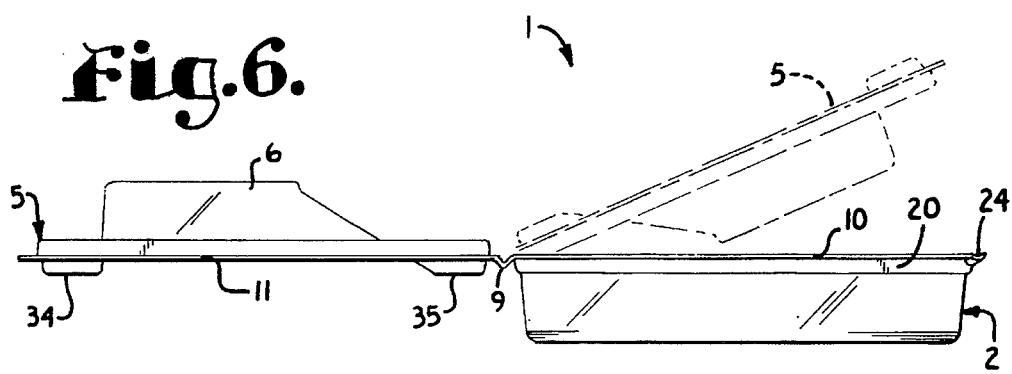
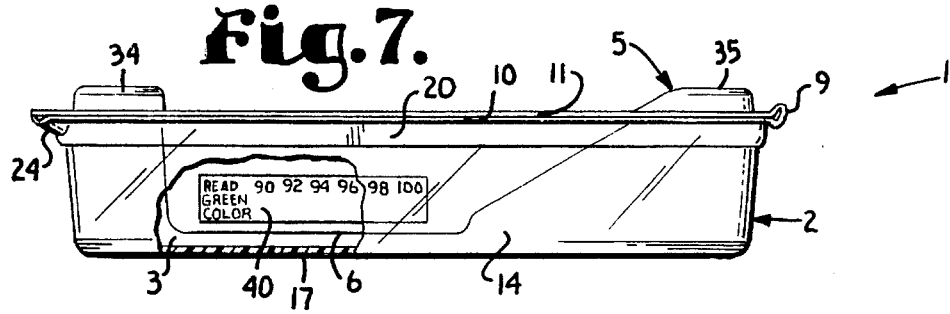
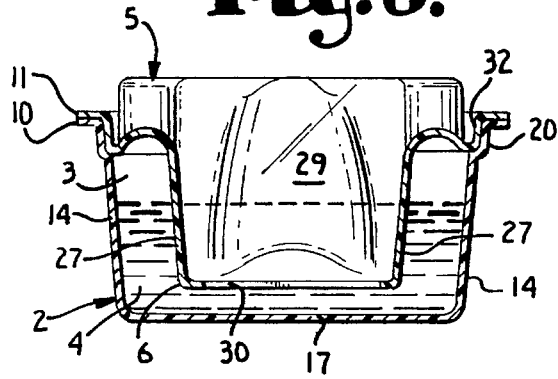

URINE SPECIMEN COLLECTION RECEPTACLE

BACKGROUND OF THE INVENTION

Drug use screening or "drug testing" is common in certain occupations, particularly those affecting public safety, as a measure to reduce drug impairment on the job and to avoid liabilities associated with hiring job applicants who are drug users. The typical procedure is to obtain a urine sample from the employee or job applicant and to perform chemical procedures on the sample which indicate the presence in the sample of unique metabolites formed by physiological processing of certain drugs.

Two important issues arise in drug testing: integrity of the test procedure and privacy considerations of the individuals being tested. Regarding integrity of the testing, it is necessary that an obtained sample not be tampered with, that it be associated with the correct "donor" that an accurate analysis be made of the sample, and that the results be accurately reported for the correct donor. Privacy considerations arise because of individuals' reluctance to produce a urine sample on demand, especially if under the observation of a monitor.

Because of occupational and, possibly, legal liabilities which can ensue from a positive drug test, it is necessary to ensure a verifiable chain of custody of urine specimens from the donor to the testing laboratory and to perform an accurate chemical analysis of the sample. The most accurate method for analyzing a urine sample for trace substances is by gas chromatograph/mass spectrometry (GC/MS). However, GC/MS is relatively expensive. Because drug testing is often carried out in large numbers, a more economical type of initial screen is usually performed, such as an enzyme multiplied immunoassay test (EMIT). Thereafter, a GC/MS analysis is performed only if the initial screen indicates the presence of one of the types of drugs tested for. In order to provide the capability of repeating the analysis of a sample should the results be challenged, it is common to divide a urine sample into two containers. Normally, the second container is identified and stored for a period of time only if the first portion of the sample tests positive.

It is generally desirable to allow an individual to produce a urine sample in privacy if adequate measures can be taken to either prevent sample tampering or to detect if tampering has occurred. However, some individuals have attempted to subvert the integrity of drug tests by the substitution of urine from others, by diluting a sample, by the addition of substances to mask drug related metabolites, and the like. In the area of tamper prevention, it is common to require donors to take off coats and leave brief cases, purses, and the like out of the room where the sample is to be produced. If such a room is a restroom or the like, it is common to place a dye in toilets and to secure faucets to discourage or prevent samples from being diluted by water from these sources. A commonly used method for detecting if a sample has been substituted or diluted is to measure the temperature of the sample. Normally, a freshly produced urine sample will have a temperature close to the average human body core temperature. Thus, if the measured temperature of a sample is outside a given range within a given period after sample production, tampering is suspected.

Because of the costs involved in employing reusable urine collection containers and then sterilizing same for reuse, disposable devices are preferred for urine specimens in drug testing. Although a male donor can conveniently produce a urine sample in a vial or bottle type container, with a portion poured into a second container for splitting the sample, this procedure is not generally convenient for female donors. For economic reasons, it would be preferred to provide a type of urine collection receptacle for use by either male and female donors. Additionally, bottle type containers do not always pour "neatly" that is without a portion spilling over the rim of the pouring container.

SUMMARY OF THE INVENTION

The present invention provides an inexpensive, disposable, unisex urine specimen collection receptacle for drug testing use which includes an inexpensive but accurate temperature indicating device and which has integral spouts formed thereon to facilitate pouring the sample into other containers.

The receptacle is a one piece unit shaped from transparent sheet or film plastic, as by vacuum forming and die cutting process. The receptacle includes a rectangular outer trough forming a urine reservoir and a lid having an integral funnel. The lid is folded about a fold line or hinge to position the funnel within the reservoir. Adjacent corners of the trough opposite the fold line have grooves therein forming spouts. Corners of the lid corresponding to the corners of the trough having the spout grooves are beveled to provide triangular openings for cooperation with the spouts to pour the collected urine into other containers without spilling.

The temperature indicating device is a liquid crystal strip type device which is inaccessibly mounted on an inside wall of the funnel for reading through a wall of the trough. The temperature indicating device has liquid crystal regions thereon which are labeled with a range of temperatures, and the temperature of the urine sample can be determined by changes in color of the regions. Peripheral flanges of the trough and lid may be sealed, as by ultrasonic welding, to retain liquids within the receptacle and to prevent access to the temperature indicating strip. The lid is provided with a bulge which forms an extension of the reservoir to resist a tendency of the urine sample to backflow and spill through an opening of the funnel when the sample is being poured into another container.

OBJECTS AND ADVANTAGES OF THE INVENTION

The principal objects of the present invention are: to provide an improved receptacle for collection of urine samples for drug testing purposes; to provide such a receptacle which is disposable and which is adapted for use by male and female donors; to provide such a receptacle including a sample temperature indicator strip positioned within the receptacle where it is inaccessible to the donor, the indicated temperature being read external to the receptacle; to provide such a receptacle which is formed of an inexpensive material by inexpensive manufacturing processes; to provide such a receptacle which is formed from a transparent sheet resin, as by a vacuum forming process followed by die cutting; to provide such a receptacle including an elongated rectangular trough forming a urine reservoir which is integrally connected by a folding hinge to a lid structure having a funnel formed therein, the lid being folded into substantially covering relation to the trough with the funnel received within the reservoir; to provide such a receptacle wherein peripheral flanges of the lid and trough are sealed, as by ultrasonic welding, to reduce spillage of the sample; to provide such a receptacle including a convex or outwardly bulged area on an outer end of the lid which effectively increases the volume of the reservoir during pouring of the sample into other containers to thereby reduce the likelihood of backflow of the sample through the funnel during pouring; to provide such a receptacle having spout grooves formed in the outer corner edge areas of the trough and bevels at corresponding corners of the lid to facilitate pouring the sample into other containers; and to provide such a urine collection receptacle which is economical to manufacture, convenient in use, and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification, include exemplary embodiments of the present invention, and illustrate various objects and features thereof.

BRIEF DESCRIPTION OF THE DRAWINGS

FIG. 1 is a perspective view of urine specimen collection device embodying the present invention.

FIG. 2 is a front end elevational view of the urine specimen collection device.

FIG. 3 is a rear end elevational view of the urine specimen collection device.

FIG. 4 is a longitudinal sectional view taken on line 4—4 of FIG. 3 and illustrates internal details of the urine specimen collection device.

FIG. 5 is a top plan view of the urine specimen collection device.

FIG. 6 is a side elevational view of the device of the present invention at a reduced scale and illustrates the collection device in an unfolded orientation with a partially folded position of a lid portion shown in phantom lines.

FIG. 7 is a side elevational view of the device with a portion of a side wall of a lower trough broken away to illustrate an inaccessible temperature indicating member of the device.

FIG. 8 is an enlarged transverse sectional view taken on line 8—8 of FIG. 4 and illustrates further internal details of the urine specimen collection device.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail:

The reference numeral 1 generally designates a urine specimen collection receptacle embodying the present invention. The receptacle i is adapted for one-time use by male or female donors as a container in which a urine sample will be produced. The sample will thereafter be transferred to a sealable container (not shown), or pair of containers for split sample procedures, and sent to a laboratory for "drug testing" that is for analysis to determine the presence of metabolites associated with certain types of illegal drugs.

The receptacle 1 generally includes an elongated trough or outer pan 2 forming a reservoir 3 for a urine sample 4 and a cooperatively shaped lid member 5 having a funnel 6 formed therein. The lid 5 is positioned in substantially closing relationship to the trough 2 with the funnel 6 positioned within the trough 2 and in fluid communication with the reservoir 3. As illustrated in FIG. 6, the receptacle 1 is preferably formed as a one-piece unit, as from a transparent resin sheet or film stock by a vacuum forming process followed by die cutting. The trough 2 and lid 5 are connected by a hinge or fold area 9, about which the lid 5 is folded to assemble the receptacle 1. The trough 2 has a peripheral flange 10 while the lid 5 has a peripheral flange 11. The lid 5 is secured to the trough 2, as by ultrasonic welding of the flanges 10 and 11. This additionally controls leakage past the flanges 10 and 11, as during pouring of the sample 4 into another container.

The trough 2 is formed by opposite side walls 14, a front end wall 15, a rear end wall 16, and a bottom wall 17. A peripheral shoulder rim 20 extends along upper edges of the walls 14–16 and connects the flange 10 to the walls 14–16. The front "corners" 22 of the trough flange 10 and shoulder rim 20 have spout grooves (FIG. 5) formed therein which fluidically communicate with the reservoir 3.

The funnel 6 is formed by opposite funnel side walls 27, a front funnel wall 28, and a rear funnel wall 29. The side and front walls 27 and 28 are positioned at a slight angle from vertical, while the rear wall 29 is at a pronounced angle, as illustrated in FIG. 4. The lower ends of the funnel walls 27–29 define a lower funnel opening 30 which, in the assembled receptacle 1, is spaced above the bottom trough wall 17.

A peripheral recessed shoulder 32 extends about the lid 5 and connects the funnel walls 27–29 with the flange 11 of the lid 5. The shoulder 32 is sized and shaped to be received within the shoulder rim 20 of the trough 2. Front and rear convex areas or bulges 34 and 35 are formed respectively between the front and rear funnel walls 28 and 29 of the funnel 6 and the recessed shoulder 32. The bulges 34 and 35 effectively extend the volume of the reservoir 3 and, to some extent, control sloshing of the sample 4 within the reservoir 3. The additional volume provided by the front bulge 34, in particular, helps to avoid backflow of the sample 4 through the funnel opening 30 when the receptacle 1 is tilted forward to pour the sample 4 into another container. Front corner areas of the lid 5, corresponding to the front corners 20 of the trough 2, are provided with bevels 37 (FIG. 5) to provide openings which cooperate with the spout grooves 22 of the trough 2 for pouring the sample 4 into another container.

In order to detect the dilution of a sample 4, or the substitution of another's urine for the sample 4, means are provided for measuring the temperature of the sample 4. The illustrated receptacle I is provided with a temperature indicating strip 40 which is adhesively applied to a side wall 27 of the funnel 6 within the reservoir 3, where it is inaccessible to the donor. The strip 40 is preferably a liquid crystal type of temperature indicator, a type which is notably accurate. The strip 40 is also preferably capable of indicating a range of temperatures at, above, and below the expected temperature of freshly produced urine. The illustrated temperature indicating strip 40 shows a temperature range of 90° F. to 100° F. in 2° F. increments.

Drug testing guidelines generally require a minimum sample volume of about 45 to 60 milliliters (about 1.5 to 2 fluid ounces). The reservoir 3 of the receptacle 1 has such a volume capacity, and the temperature indicating strip 40 is positioned on the side wall 27 of the funnel 6 within the reservoir 3 at a location to be directly immersed by a sample 4 of the required volume. As positioned, the strip 40 can be read through the corresponding trough side wall 14, which is transparent. For the sample temperature to be a reliable indicator of authenticity of the sample 4, it must be read within a specified time period (on the order of four minutes) after sample production.

It is to be understood that while certain forms of the present invention have been illustrated and described herein, it is not to be limited to the specific forms or arrangement of parts described and shown.

What is claimed and desired to be secured by Letters Patent is as follows:

1. A body fluid collection device comprising:
   (a) an outer trough forming a body fluid reservoir;
   (b) an inner lid including funnel means;
   (c) said lid being received on said trough to substantially close said trough and with said funnel means positioned within said trough to direct a fluid from said funnel means into said reservoir;
   (d) spout means formed on an edge of said trough to facilitate pouring a fluid from said reservoir to another container;
   (e) said trough being rectangular and having corner areas; and
   (f) said spout means being formed at one of said corner areas.

2. A device as set forth in claim 1 wherein:
   (a) said trough and said lid are formed as a one piece structure with a fold area separating a trough portion from a lid portion; and
   (b) said lid portion is positioned on said trough portion by folding said lid portion about said fold area into a received relationship within said trough portion.

3. A device as set forth in claim 2 wherein:
   (a) said one piece structure is formed by shaping a synthetic resin sheet material.

4. A device as set forth in claim 2 wherein:
   (a) said one piece structure is shaped by vacuum forming a synthetic resin sheet material.

5. A device as set forth in claim 2 wherein:
   (a) said trough and said lid are formed of a transparent material.

6. A device as set forth in claim 1 and including:
   (a) a temperature indicating device positioned within said reservoir to indicate a temperature of a body fluid collected in said reservoir.

7. A device as set forth in claim 1 wherein:
   (a) said lid includes an enlargement forming a pouring reservoir to reduce backflow of a collected fluid through said spout means during pouring to another container.

8. A urine collection device comprising:
   (a) an outer trough defined by trough walls and forming a urine reservoir;
   (b) an inner lid including funnel means;
   (c) said trough and said lid being formed as a one piece structure with a fold line separating a trough portion from a lid portion;
   (d) said lid portion being received on said trough portion to substantially close said trough and with said funnel means positioned within said trough to direct urine from said funnel means into said reservoir by folding said lid portion about said fold line into a received relationship within said trough portion;
   (e) said one piece structure being formed by shaping a transparent synthetic resin sheet material;
   (f) a temperature indicating device inaccessibly positioned on a surface of said funnel means within said reservoir whereby said temperature indicating device can be read through of one of said troughs;
   (g) spout means formed on an edge of said trough to facilitate pouring urine collected in said reservoir to another container; and
   (h) said funnel means having an opening located substantially below said spout means.

9. A device as set forth in claim 8 wherein:
   (a) said one piece structure is shaped by vacuum forming said synthetic resin sheet material.

10. A device as set forth in claim 8 wherein:
    (a) said lid includes an enlargement forming a pouring reservoir to reduce backflow of collected urine through said spout means during pouring to another container.

11. A urine collection device comprising:
    (a) a rectangular outer trough defined by trough walls and forming a urine reservoir, said trough having corner areas;
    (b) an inner lid including funnel means;
    (c) said trough and said lid being formed as a one piece structure with a fold line separating a trough portion from a lid portion;
    (d) said lid portion being received on said trough portion to substantially close said trough and with said funnel means positioned within said trough to direct urine from said funnel means into said reservoir by folding said lid portion about said fold line into a received relationship within said trough portion;
    (e) said one piece structure being shaped by vacuum forming a transparent synthetic resin sheet material;
    (f) a temperature indicating device inaccessibly positioned on a surface of said funnel means within said reservoir whereby said temperature indicating device can be read through one of said trough walls; and
    (g) spout means formed on an edge of said trough at an adjacent pair of said corner areas to facilitating pouring urine collected in said reservoir to another container.

12. A device as set forth in claim 11 wherein:
    (a) said lid includes an enlargement forming a pouring reservoir to reduce backflow of collected urine through said spout means during pouring to another container.

13. A urine collection device comprising:
    (a) an outer trough defined by trough walls and forming a urine reservoir;
    (b) an inner lid including funnel means;
    (c) said trough and said lid being formed as a one piece structure with a fold line separating a trough portion from a lid portion;
    (d) said lid portion being received on said trough portion to substantially close said trough and with said funnel means positioned within said trough to direct urine from said funnel means into said reservoir by folding said lid portion about said fold line into a received relationship within said trough portion;
    (e) said one piece structure being formed by shaping a transparent synthetic resin sheet material;

(f) a temperature indicating device inaccessibly positioned on a surface of said funnel means within said reservoir whereby said temperature indicating device can be read through of one of said troughs;

(g) spout means formed on an edge of said trough to facilitate pouring urine collected in said reservoir to another container;

(h) said trough being rectangular and having corner areas; and (i) said spout means being formed at an adjacent pair of said corner areas opposite said fold line.

* * * * *